United States Patent [19]

Mears

[11] 4,454,876
[45] Jun. 19, 1984

[54] PELVIC FIXATION PLATE AND METHOD OF IMPLANTING SAME

[75] Inventor: Dana C. Mears, Oakmont, Pa.

[73] Assignee: University of Pittsburgh, Pittsburgh, Pa.

[21] Appl. No.: 381,703

[22] Filed: May 25, 1982

[51] Int. Cl.³ .......................... A61F 5/04; A61B 17/18
[52] U.S. Cl. .................................................. 128/92 D
[58] Field of Search ............... 128/92 D, 92 R, 92 B, 128/92 BA, 92 E, 92 G, 84 R, 69

[56] References Cited

U.S. PATENT DOCUMENTS

| 3,463,148 | 8/1969 | Treace | 128/92 |
|---|---|---|---|
| 3,741,205 | 6/1973 | Markolf et al. | 128/92 B |
| 4,024,860 | 5/1977 | Chelnokov et al. | 128/84 R |
| 4,038,704 | 8/1977 | Ring | 3/1.91 |
| 4,185,623 | 1/1980 | Volkov et al. | 128/69 |
| 4,219,015 | 8/1980 | Steinemann | 128/92 D |

FOREIGN PATENT DOCUMENTS

| 2233973 | 1/1975 | France | 128/92 D |
|---|---|---|---|
| 2254304 | 7/1975 | France | 128/92 D |

OTHER PUBLICATIONS

Bone Plates–Sherman-Type Plates, Vitallium Surgical Appliances (Catalog), Mar. 1948, p. 7.
Orthopaedic Bone Plating, Orthopaedic Catalogue, Twentieth Edition, Down Bros. and Mayer & Phelps, Ltd, p. G55.
"Potentiel Application of Graphite Fiber and Methyl Methacrylate Resin Composites as Internal Fixation Plates" by Woo et al, J. Biomed. Materials Res. vol. 8, pp. 321–338, 1974.
Product Encyclopedia, Zimmer–USA, 1978 pp. B168 and B169.

Primary Examiner—Ronald L. Frinks
Attorney, Agent, or Firm—Buell, Blenko, Ziesenheim & Beck

[57] ABSTRACT

An implantable pelvic fixation plate having an elongated body provided with a central portion and a pair of iliac supporting portions disposed on opposite sides of said central portion. Said iliac supporting portions having a greater average transverse width than the average transverse width of said central portion and said iliac supporting portions having at least one opening therethrough. The iliac supporting portions and central portion may be generally plate-like with the iliac supporting portions projecting generally downwardly and outwardly with respect to the central portion. In a preferred embodiment, the iliac supporting portions will have an axial extent which is about 65 to 125 percent of the axial extent of the central portion and will form a larger included angle of about 100 to 140 degrees with respect to a plane passing through the central portion. The pelvic fixation plate preferably is of unitary construction. A method of implanting the pelvic fixation plate in repairing a pelvic ring by positioning the iliac supporting portions adjacent to the patient's iliac bones and securing the iliac supporting portions to the bones as by fasteners passing through the iliac supporting portions.

13 Claims, 8 Drawing Figures

PELVIC FIXATION PLATE AND METHOD OF IMPLANTING SAME

BACKGROUND OF THE INVENTION

1. Field of the Invention

This invention relates to an implantable pelvic fixation plate and a method of employing the same in repairing a pelvic ring.

2. Description of the Prior Art

Various means have been known to treat damage to skeletal portions of humans and animals for skeletal deficiencies resulting from traumatic injuries, diseases, birth defects, deterioration with age and deterioration from other causes. It has been known to employ external means such as casts, splints and external fixation apparatus. It is also been known to use various forms of implantable prostheses. See, for example, U.S. Pat. No. 4,038,704. Implantable members employed for bone fixation have also been known. See, for example, U.S. Pat. Nos. 3,463,148; 3,741,205 and 4,219,015.

Very little has been known in respect of effective means ffor treating fracture, comminution or other deterioration of the posterior aspect of the pelvic ring.

U.S. Pat. No. 4,024,860 discloses apparatus actuated by compressed gas in fixing the pelvic halves on pubic symphysis ruptures. In general, the disclosure comtemplates providing a pair of elastic members which engages the patient's body and, with the cooperation of a servomechanism coupled to a power source exerts a compressive force on the patient's body.

U.S. Pat. No. 4,185,623 discloses apparatus for hip joint restoration wherein a pelvic yoke is said to provide both relief of the hip joint and permit mobility of the same. A first yoke is secured to the upper portion of the ilium and a second yoke is secured to the thigh. Various guides and traction wires are employed to permit the various degrees of freedom desired for the hip joint.

There remains, therefore, a very real and substantial need for a pelvic fixation plate which may be implanted in order to restore the pelvic ring when the posterior aspect of the pelvic ring has suffered deterioration or damage.

SUMMARY OF THE INVENTION

The present invention has solved the above described problem.

An implantable pelvic fixation plate has an elongated body provided with a central portion and a pair of iliac supporting portions disposed on opposite sides thereof. The iliac supporting portions have a greater average transverse width than the average transverse width of the central portion, have at least one fastener receiving opening and are preferably generally angularly downwardly and outwardly disposed with respect to the central portion. Certain predetermined relative sizes of the central portion and iliac supporting portions and relative angular positions contribute to the desired relationships. The iliac supporting portions preferably are generally diamond shaped and terminate in a generally straight edge which is oriented substantially perpendicularly with respect to the longitudinal axis of the fixation plate.

The fixation plate is preferably of unitary construction. It is preferably made of any material having suitable inertness, strength and formability. It may advantageously be made of a material selected from the group consisting of stainless steel, titanium, alloys thereof and fiber reinforced composites including graphite-graphite composites, and polymer graphite composites. A suitable polymer graphite composite is a polyethylene graphite composite.

In the method of repairing a damaged pelvic ring using the fixation plate of the present invention, the plate is positioned with the iliac supporting portions adjacent to the patient's iliac bones and securement of the respective iliac supporting portions to the bones is effected. This may be advantageously be accomplished by means of mechanical fasteners.

It is an object of the present invention to provide an implantable pelvic fixation plate which is adapted to establish structural integrity of a damaged pelvic ring.

It is a further object of the present invention to provide such a pelvic fixation plate which is adapted to effectively immobilize a pelvis which has had damage or deterioration in the posterior aspects.

It is another object of the present invention to provide a simple and economical means for repairing posterior damage to the pelvic ring.

It is another object of the present invention to provide a method of repairing a pelvis employing a pelvic fixation plate of the present invention.

These and other objects of this invention will be fully understood from the following description of the invention on reference to the illustrations appended hereto.

DESCRIPTION OF THE PREFERRED EMBODIMENTS

Figure 1:
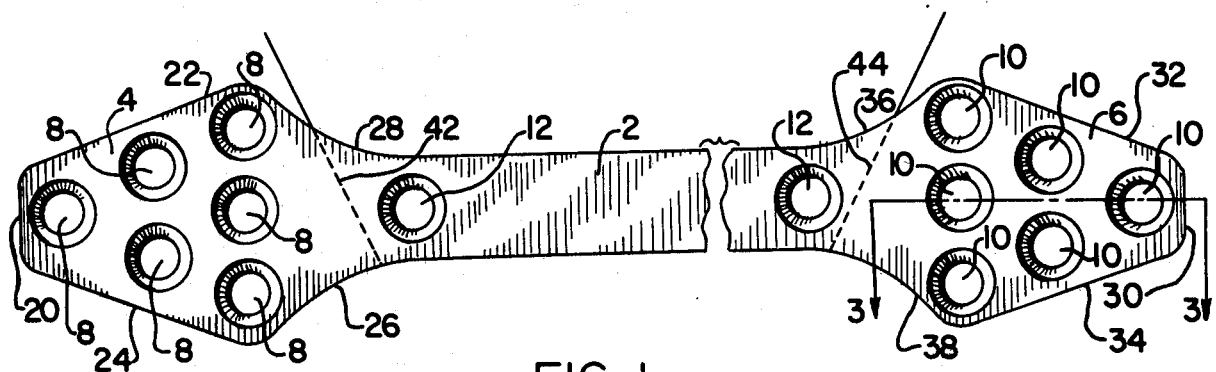
FIG. 1 is a fragmented top plan view of a form of pelvic fixation plate of the present invention.
Figure 2:
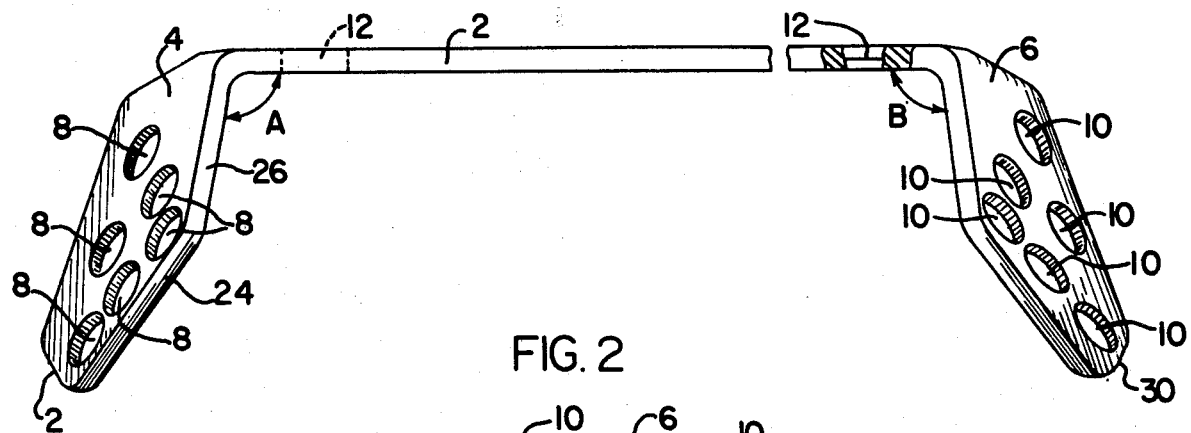
FIG. 2 is a fragmented front elevational view of the fixation plate shown in FIG. 1 with the iliac supporting portions angularly disposed.

Referring now in greater detail to FIGS. 1 and 2, there is shown a form of pelvic fixation plate of the present invention. The plate has a central portion 2 (which has been broken away for clarity of illustration as it may have any desired lenggth to suit the needs of a specific patient). Disposed on opposite ends of the central portion 2 are a pair of iliac supporting portions 4, 6 which are adapted to be secured to the iliac bones of the patient. Both the central portion 2 and the iliac supporting portions 4, 6, in the form shown, are plate-like in nature with the iliac supporting portions 4, 6 having a greater average transverse extent than the central portion 2.

In the form illustrated, iliac supporting portion 4 is provided with a plurality of holes 8 and iliac supporting portion 6 is provided with a plurality of holes 10. These holes 8, 10 serve as means for securing the iliac supporting portions 4, 6 to the iliac bones of the patient. Such securement may conveniently be effected by mechanical fasteners such as screws, for example, or other suitable means. It will be noted that central portion 2 also is provided with holes 12 which facilitate anchoring of the plate to the patient as by mechanical fasteners.

In the form illustrated, it will be noted that the iliac supporting portions 4, 6 have, respectively, blunt ends 20, 30 which provide generally flat edges oriented substantially perpendicularly with respect to the longitudinal axial direction of central portion 2.

Iliac supporting portion 4 has a pair of sidewalls 22, 24 which at one end connect to end 20 and diverge generally toward central portion 2. It also has sidewalls 26, 28 which converge toward central portion 2 and connect the diverging sidewalls 22, 24 to the central portion 2. Similarly, iliac supporting portion 6 has diverging sidewalls 32, 34 which originate with end wall 30 and connect with sidewalls 36, 38 which converge toward central portion 2.

As is shown generally in FIG. 2 the iliac supporting portions generally are oriented downwardly and outwardly with respect to central portion 2. Iliac supporting portion 4 assumes an angle A with respect to central portion 2 and iliac supporting portion 6 assumes an angle B with respect to central portion 2. These angles, which may be equal preferably, are about 100 to 140 degrees. It will be noted, that in addition to being angularly disposed with respect to a plane running through central portion 2 at angles A, B, the iliac supporting portions also are not axially aligned (When deformed as shown in FIG. 2 as distinguished the planar version shown, before bending of the iliac supporting portion 4, 6, in FIG. 1) with the central longitudinal axis of central portion 2.

It will be appreciated, that in this fashion, by selecting the proper length for central portion 2 and the proper position for each of the iliac supporting portions 4, 6, one may provide effective and intimate support for the iliac bones of the patient and such engagement may be effectively maintained through the use of mechanical fasteners passing through openings 8, 10. Screws such as cortical or cancellous screws may be employed, for example.

Figure 3:
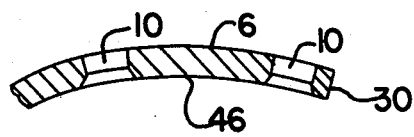
FIG. 3 is a cross-sectional illustration of a form of iliac supporting portion of the pelvic fixation plate of FIG. 1 taken through 3—3.

FIG. 3 illustrates a preferred feature of the invention wherein the iliac supporting portion 6 defines a downwardly facing concave sector 46 so as to facilitate more intimate engagement between the iliac supporting portion and the iliac bone of the patient.

Figure 4:
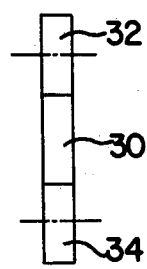
FIG. 4 is an end elevational view of the pelvic fixation plate of FIG. 1.

FIG. 4 shows an end elevational view of the platelike member shown in FIG. 1 prior to deformation of the structure to define the shape shown in FIG. 2. In effecting such bending iliac supporting portion 4 is bent along bend line 42 and iliac supporting portion 6 is bent along bend line 48. These bend lines preferably formed angles with respect to the longitudinal axis of the central portion 2 of about 15 to 25 degrees.

In the underformed state shown in FIGS. 1 and 4 the combined axial extent of the iliac supporting portions 4, 6 measured along the surface thereof is about 65 to 125 percent of the axial extent of the central portion 2. It may be desirable to provide the plate in a number of different sizes by providing plates with central portions of different axial extent.

Figure 5:
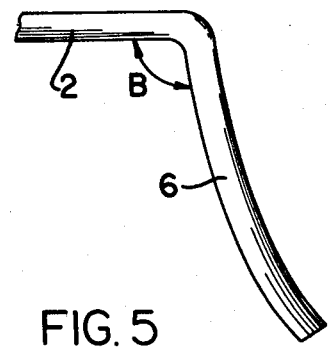
FIG. 5 is a fragmentary illustration of a portion of the fixation plate of FIG. 1.

Referring now to FIG. 5, there is shown a fragmentary detail of the angle B between the central portion 2 and the iliac supporting portion 6.

Figure 6:
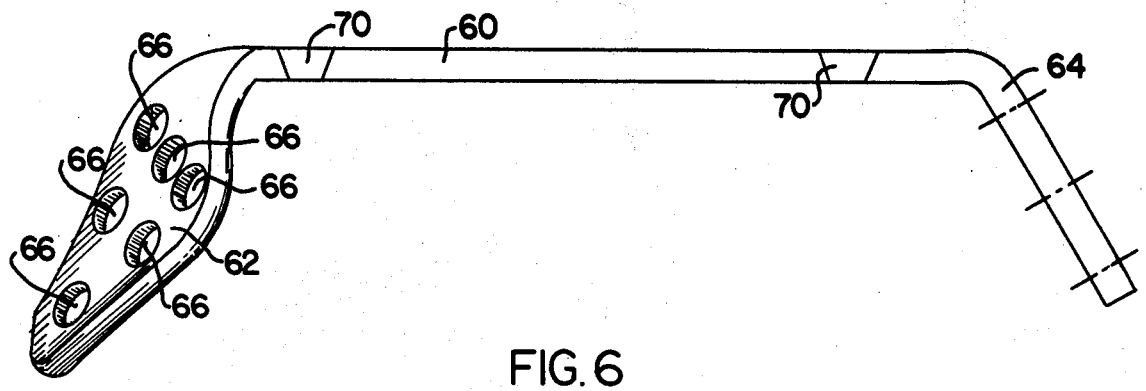
FIG. 6 is a front elevational view of another form of pelvic fixation plate of the present invention.
Figure 7:
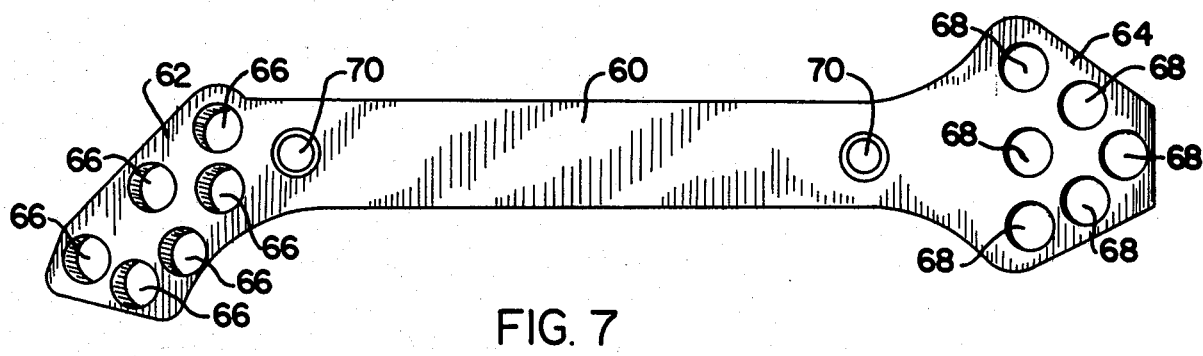
FIG. 7 is a top plan view of the pelvic fixation plate of FIG. 6.
Figure 8:
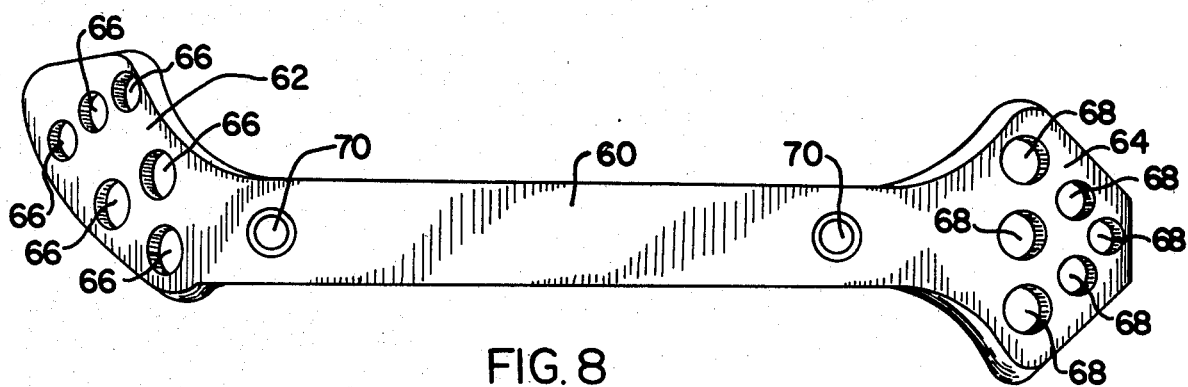
FIG. 8 is a bottom plan view of the pelvic fixation plate of FIG. 6.

Referring now to FIGS. 6 through 8, a modified embodiment of the invention will be considered. In this embodiment a central portion 60 cooperates with iliac supporting portions 62, 64 which have respectfully, a series of holes 66, 68. Central portion 60 is provided with holes 70.

As is shown in FIG. 6, angularly downwardly projecting iliac supporting plate 64 is connected to the central portion 60. In this embodiment the iliac supporting plate 62 on one side has been rotated out of axial alignment with respect to the central longitudinal axis of central portion 60, while the other iliac supporting plate 64 has its longitudinal axis generally aligned with the longitudinal axis of central portion 60.

In the method of the present invention, one may employ the unique pelvic fixation plate of the present invention by positioning the same with each iliac supporting portion being disposed adjacent to the patient's iliac bones and securing these iliac supporting portions to the iliac bones. Such securement may readily be effected by providing mechanical fasteners such as screws which would pass through the openings and into the bones. It will be appreciated that prior to securement of the pelvic fixation plate to the patient one must select a plate which is properly proportioned so as to conform to the spacing or desired spacing of the iliac bones. The bending of the iliac supporting plates may be accomplished at the time and place of manufacture, at the institution where the implant is being performed prior to the procedure or during the procedure immediately prior to insertion. Bending or final bending may be accomplished by cold forming in the operating room by a bending press, if desired.

It will be appreciated, therefore, that the present invention provides a solution to a significant, longstanding problem in respect of restoration of the integrity of the pelvic ring and is particularly useful in respect to posterior aspect restoration. All of this is accomplished in a simple, economical and durable fashion.

Whereas particular embodiments of the invention have been described above for purposes of illustration, it will be evident to those skilled in the art that numerous variations of the details will be made without departing from the invention as defined in the appended claims.

I claim:

1. An implantable pelvic fixation plate comprising an elongated body having a central portion and a pair of iliac supporting portions disposed on opposed sides of said central portion, said iliac supporting portions each having at least one fastener receiving opening, said iliac supporting portions having a greater average transverse width than the average transverse width of said central portion, said iliac supporting portions and said central portion each being generally plate-like, said iliac supporting portions projecting downwardly and outwardly with respect to said central portion, and a plane passing through said central portion forms a larger included angle of about 100 to 140 degrees with respect to each said iliac supporting portion.

2. The pelvic fixation plate of claim 1 including said iliac supporting portions being generally diamond shaped.

3. The pelvic fixation plate of claim 1 including the combined axial extent of said iliac supporting portions measured along the surface thereof being about 65 to 125 percent of the axial extent of said central portion.

4. The pelvic fixation plate of claim 3 including
said central portion having a pair of spaced openings passing therethrough.

5. The pelvic fixation plate of claim 1 including
said iliac supporting portions terminating in generally straight free ends which are oriented generally perpendicularly withh respect to the longitudinal axis of said central portion.

6. The pelvic fixation plate of claim 5 including
said iliac supporting portions having first lateral edges which diverge towards said central portion and second lateral edges which converge towards said central portion.

7. The pelvic fixation plate of claim 1 including
said body being of unitary construction.

8. The pelvic fixation plate of claim 7 including
said body composed of a material selected from the group consisting of
stainless steel, titanium, alloys thereof and fiber reinforced composites.

9. An implantable pelfic fixation plate comprising
an elongated body having a central portion and a pair of iliac suppoting portions disposed on opposed sides of said central portion,
said iliac supporting portions each having at least one fastener receiving opening,
said iliac supporting portions having a greater average transverse width than the average transverse width of said central portion,
said iliac supporting portions being generally plate-like,
said iliac supporting portions projecting downwardly and outwardly with respect to said central portion,
a plane passing through said central portion forms a larger included angle of about 100 to 140 degrees with respect to each said iliac supporting portion, and
the bend lines between said central portion and said iliac supporting portion forming an angle of about 15 to 25 degrees with respect to the longitudinal axis of said central portion.

10. The pelvic fixation plate of claim 9 including
a first said bend line being disposed at a different said angle with respect to said longitudinal axis then a second said bend line.

11. A method of repairing a pelvic ring comprising
providing a plevic fixation plate having a central portion and a pair of laterally enlarged iliac supporting portions disposed generally angularly with respect to said central portion with each said iliac supporting portion having at least one opening therein,
positioning said iliac supporting portions adjacent to patient's iliac bones, and
securing said iliac portions to said iliac bones.

12. The method of pelvic repair of claim 11 including
securing said iliac supporting portions to said said iliac bones by passing mechanical fasteners through openings in said iliac supporting portions and into said bones.

13. The method of pelvic repair of claim 12 including
prior to said positioning of said pelvic fixation plate selecting the length of said plate and the relative angular position of said iliac positioning plates so as to have predetermined relationship to the relative positions of said iliac bones of said patient.

* * * * *

UNITED STATES PATENT AND TRADEMARK OFFICE
CERTIFICATE OF CORRECTION

PATENT NO. : 4,454,876
DATED : June 19, 1984
INVENTOR(S) : DANA C. MEARS

It is certified that error appears in the above-identified patent and that said Letters Patent is hereby corrected as shown below:

Column 1, line 23, "ffor" should be --for--.

Column 2, line 57, "lenggth" should be --length--.

Claim 5, column 5, line 11, "withh" should be --with--.

Claim 9, column 5, line 28, "suppoting" should be --supporting--.

Signed and Sealed this

Thirteenth Day of November 1984

[SEAL]

Attest:

GERALD J. MOSSINGHOFF

Attesting Officer

Commissioner of Patents and Trademarks